United States Patent
Forster et al.

(10) Patent No.: US 9,907,678 B2
(45) Date of Patent: Mar. 6, 2018

(54) PROSTHESIS SOCKET

(71) Applicant: OTTO BOCK HEALTHCARE GMBH, Duderstadt (DE)

(72) Inventors: Heiko Forster, Duderstadt (DE); Christian Heublein, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 14/424,382

(22) PCT Filed: Aug. 22, 2013

(86) PCT No.: PCT/EP2013/002541
§ 371 (c)(1),
(2) Date: Feb. 26, 2015

(87) PCT Pub. No.: WO2014/032785
PCT Pub. Date: Mar. 6, 2014

(65) Prior Publication Data
US 2015/0209161 A1    Jul. 30, 2015

(30) Foreign Application Priority Data

Aug. 31, 2012  (DE) .................. 10 2012 017 213

(51) Int. Cl.
*A61F 2/80* (2006.01)
*A61F 2/78* (2006.01)
*A61F 2/72* (2006.01)
(Continued)

(52) U.S. Cl.
CPC .............. *A61F 2/80* (2013.01); *A61F 2/7812* (2013.01); *A61F 2/54* (2013.01); *A61F 2/72* (2013.01);
(Continued)

(58) Field of Classification Search
CPC ........................................................ A61F 2/80
See application file for complete search history.

(56) References Cited

U.S. PATENT DOCUMENTS 5,139,523 A    8/1992  Paton et al.
8,591,599 B1 * 11/2013  Kaliki ................. A61B 5/6828
                                                              600/372
(Continued)

FOREIGN PATENT DOCUMENTS

DE       334122 C    3/1921
DE       347087 C    1/1922
(Continued)

OTHER PUBLICATIONS

U.S. Appl. No. 61/559,051, filed Nov. 12, 2011.*
PCT International Search Report for PCT International Patent Application No. PCT/EP2013/002541, dated Nov. 28, 2013.
(Continued)

*Primary Examiner* — David H Willse
(74) *Attorney, Agent, or Firm* — Holland & Hart

(57) ABSTRACT

A prosthesis socket having a proximal end and a distal end, an opening at the proximal end for the insertion of a stump, a receiving device for a prosthesis component at the distal end, and at least one splint, which includes a dimensionally stable material and which, in the area of the distal end, comprises a circular receiver. The splint is embedded in a flexible matrix of plastic or silicone. The matrix of plastic or silicone forms a hollow profiled. At least one flexible and tensionally rigid limiting element is arranged on the splint.

22 Claims, 4 Drawing Sheets

(51) Int. Cl.
*A61F 2/54* (2006.01)
*A61F 2/50* (2006.01)

(52) U.S. Cl.
CPC ............... *A61F 2002/5027* (2013.01); *A61F 2002/5055* (2013.01); *A61F 2002/5056* (2013.01); *A61F 2002/5083* (2013.01); *A61F 2002/7862* (2013.01)

(56) References Cited

U.S. PATENT DOCUMENTS

| | | |
|---|---|---|
| 2004/0158332 A1 | 8/2004 | Carstens |
| 2007/0225824 A1 | 9/2007 | Einarsson |
| 2007/0276510 A1 | 11/2007 | Becker et al. |
| 2010/0082116 A1 | 4/2010 | Johnson et al. |
| 2012/0041567 A1 | 2/2012 | Cornell |
| 2013/0123940 A1* | 5/2013 | Hurley ................ A61F 2/80 623/33 |

FOREIGN PATENT DOCUMENTS

| | | | |
|---|---|---|---|
| DE | 102010019843 A1 | 11/2011 | |
| EP | 1854621 A1 | 11/2007 | |
| FR | 2539616 A1 | 7/1984 | |
| FR | 2828093 A1 | 2/2003 | |
| SU | 1496792 A1 * | 7/1989 | ............ A61F 2/60 |

OTHER PUBLICATIONS

English Translation of Soviet Union Patent No. SU1496792; dated Jul. 30, 1989; 4 pages.

* cited by examiner

PROSTHESIS SOCKET

TECHNICAL FIELD

The invention relates to a prosthesis socket having a proximal end and a distal end with an opening at the proximal end for introducing a stump, in particular an amputation stump, and a receiving device for a prosthetic component at the distal end.

BACKGROUND

For the prosthetic treatment of a patient, the missing limbs are replaced by mechanical aids, for example by prosthetic hands, prosthetic feet and prosthetic knee joints. In order to ensure sufficient functionality, it is necessary to fasten these prosthetic components securely to the patient, preferably to a stump of a remaining limb. In the case of what is referred to as liner technology, a plastics or silicone liner is placed around the stump, a prosthesis socket then being attached thereto, for example via adhesion or negative pressure. The prosthesis socket as an external frame generally consists of a rigid material which is adapted individually to the stump of the patient. The prosthesis socket is made in that a plaster cast of the stump is taken, a positive is produced and the socket is modeled on this positive with addition of material for a liner made of a rigid plastics material or a fiber-reinforced plastics material. At the distal end of the socket, receiving devices for further prosthetic components, for example joints or prosthetic hands, are provided.

SUMMARY

It is the object of the present invention to provide a prosthesis socket which receives high acceptance even on being worn for the first time, and the socket has a natural feel as a result of its flexibility and allows direct feedback at the stump.

According to the invention, this object is achieved by a prosthesis socket having the features of the main claim; advantageous configurations and developments of the invention are disclosed in the dependent claims, the description and the figures.

In the case of the prosthesis socket according to the invention, having a proximal end and a distal end, with an opening at the proximal end for introducing a stump and a receiving device for a prosthetic component at the distal end, provision is made of at least one splint made of a dimensionally stable material, said splint comprising a circular receptacle in the region of the distal end. The splint is embedded in a flexible plastics or silicone matrix, wherein the plastics or silicone matrix forms a hollow cross section. The splint made of a dimensionally stable material, said splint having a circular receptacle in the distal region, that is to say the front region from the patient's perspective, surprisingly ensures sufficient stability of the prosthesis socket for receiving and transmitting the forces and moments which are applied to the prosthesis socket by the attached prosthetic component, for example a prosthetic hand. Via the splint, together with the circular limiting element, it is possible to introduce the forces that arise into the particular stump. As a result of the splint being embedded in the flexible plastics or silicone matrix, the position of the splint can adapt to the contour of the stump, and as a result of the formation of a hollow cross section, a more or less closed prosthesis socket having a hollow body for receiving the amputation stump and further devices such as controllers or drives is created. The complete covering with the plastics or silicone matrix results in improved protection of the stump and likewise of the prosthetic components and of the devices accommodated in the prosthesis socket. Arranged on the splint is a relatively flexible and tensionally rigid limiting element, by way of which the lengthening and displacement of the splint relative to the stump, and the expansion of the plastics or silicone matrix is limited. This avoids the situation in which, in the case of an incorrect selection of the prosthesis socket or of undesired excessive loading, the splint is undesirably excessively bent and possibly the plastics or silicone matrix is destroyed. Furthermore, the limiting element acts as a safeguard against undesired loss. The limiting element can be configured with a variable length, and in particular can have an adjustable length, in order to be able to achieve individual adaptation of the prosthesis socket to the particular user.

In one development of the invention, provision is made for the prosthesis socket to comprise two or more splints which are arranged in a manner spaced apart from one another and are located at least regionally opposite one another. The splints are embedded in the flexible plastics or silicone matrix, wherein the plastics or silicone matrix at least regionally fills the spacing between the splints, preferably forming the hollow cross section. The two splints made of a dimensionally stable material, which are connected together in the distal region, that is to say in the region remote from the body from the patient's perspective, improve the stability of the prosthesis socket in the reception and transmission of the forces and moments which are applied to the prosthesis socket by the attached prosthetic component. Via the splints, it is possible to introduce the forces in a targeted manner into the particular stump. The splints are arranged in a manner spaced apart from one another and are located at least partially opposite one another, and so the stump of the limb is clasped and held in a clamp-like manner at least on two sides. The embedding of the splints in a flexible plastics or silicone matrix ensures that the splints are associated with one another, and wearing comfort is likewise increased. As a result of the embedding of the splints in the flexible plastics or silicone matrix, the splints are displaceable relative to one another, and so adaptation to different stump contours is possible. Requirements concerning an individual visual appearance can be met more easily. Since the plastics or silicone matrix at least regionally fills the spacing between the splints, forming a hollow cross section, a more or less closed prosthesis socket having a stable hollow body is created. The circumferentially complete covering of the splints with the plastics or silicone matrix results in improved protection for the stump. In the case of the configuration of the prosthesis socket with a plurality of rails, the limiting element can be arranged between the splints and fastened thereto such that the lengthening and displacement of the splints with respect to one another is limited.

Provision is made for the plastics or silicone matrix to complete fill the spacing between the splints, in particular completely fill said spacing from the distal end, forming a hollow cross section. The configuration in which the formation of a closed hollow cross section occurs along the entire length of the splints is particularly preferred. In a configuration as a forearm socket, in order to ensure sufficient movability, ventral and dorsal cutouts or set-backs can be provided in the plastics or silicone matrix, so that bending or stretching movements are possible without restrictions.

In one development of the invention, provision is made for the splint or splints to be connected at the distal end to a closed ring or to be formed in one piece, forming a closed ring. The formation of a closed ring at the distal end allows a stable configuration of the distal end by the dimensionally stable splint or splints or a suitable ring material. In addition to the usually preferred light metals, it is possible and provision is made for both the splints and the closed ring to be formed from a fiber-reinforced plastics material, for example carbon-fiber-reinforced plastics materials or glass-fiber-reinforced plastics materials. As a result, in addition to high strength and dimensional stability, a light weight is realized.

The plastics or silicone matrix can be formed in an elastic manner, so that displacement of the splint or splints relative to one another is possible under a restoring force. As a result of the elastic configuration of the plastics or silicone matrix, improved adaptability to and adhesion to the stump is possible.

The plastics or silicone matrix can completely surround the splint or splints, such that the splints do not bear against the surface either on the outer side of the prosthesis socket or on the inner side of the prosthesis socket, as is the case in surface embedding. This makes it possible for the prosthesis socket and thus also the prosthesis not to slip when taken off on smooth underlying surfaces and furthermore for no loud noises to occur when the prosthesis socket is put on, so that the existence of the prosthesis socket is not directly noticed by people in the vicinity.

The splint or splints can have recesses for receiving condyles in the region of the proximal end, in order to allow better force transmission to the stump. As a result, rotary movements can be transmitted more easily, in particular in the case of a forearm prosthesis.

In a configuration of the prosthesis socket having two or more splints, the latter are advantageously arranged in a manner oriented medially laterally in the fitted state of the prosthesis socket, so that when the prosthesis is used for support or taken off, only the relatively soft material of the plastics or silicone matrix comes into contact with the smooth surface. This results in improved feedback when the prosthesis is used for support, since taking off can be felt directly. In the case of only one splint, the latter is preferably arranged medially or laterally, in order to create the same effect.

A flexible and elastic inner socket can be secured to the prosthesis socket, in particular to the splint or the splints, in order to be able to realize improved wearing comfort. The inner socket can be fastened reversibly to the prosthesis socket, which then acts as an outer socket, for example via screws or the like. Via the orientation of the thread on the inner socket, it is possible to position the prosthesis socket relative to the stump.

The limiting element is preferably inserted on that side on which the greatest tensile force takes place, and can thus be attached on one side. Alternatively, the relatively flexible and tensionally rigid limiting element fastened between the splints or to the splint is circularly disposed, with the result that a favorable load transfer from the socket to the stump and vice versa can be achieved. The limiting element can consist of a flexible web which can be manufactured from a high-strength material, for example from aramid fibers, high-strength polyethylene fibers such as Dyneema, or carbon fibers. The limiting elements can be formed in a non-elastic manner.

BRIEF DESCRIPTION OF THE DRAWINGS

An exemplary embodiment of the invention is explained in more detail in the following text with reference to the appended figures, in which.

DETAILED DESCRIPTION

Figure 1:
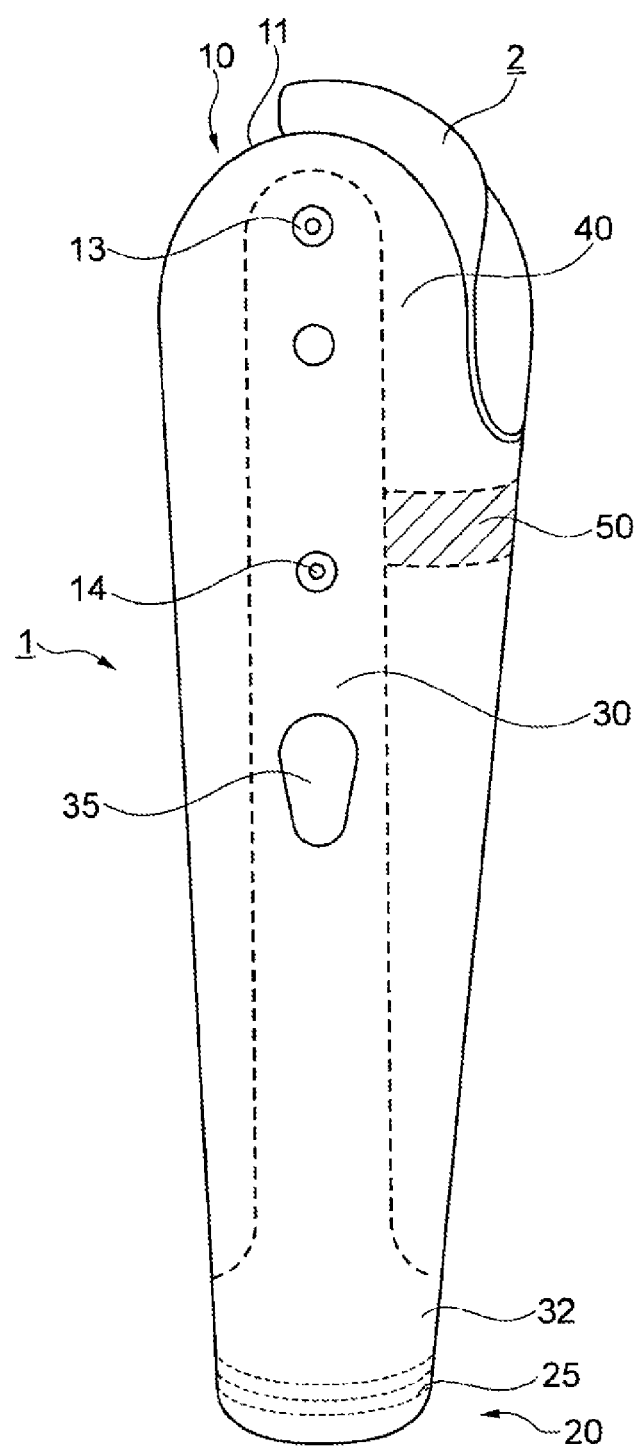
FIG. 1 shows a schematic overall view of a prosthesis socket having an inner socket.

FIG. 1 illustrates a perspective schematic illustration of a prosthesis socket 1 in the form of a forearm socket. The prosthesis socket 1 has a proximal end 10 and a distal end 20. Formed at the proximal end 10 is a distal opening 11, which can be seen better in FIG. 2. The distal opening 11 serves for the introduction of a stump (not illustrated), for the introduction of a forearm stump in the exemplary embodiment illustrated. Provided at the distal end 20 of the prosthesis socket is a receiving device 25 for a prosthetic component, for example in the form of a thread, a bayonet fitting or the like. In the exemplary embodiment illustrated, the receiving device 25 is provided for fastening a prosthetic hand.

The prosthesis socket 1 has two splints 30 extending along the longitudinal extent of the prosthesis socket 1, said splints 30 being arranged medially laterally and completely embedded in a flexible plastics or silicone matrix 40. The splints 30 extend from the proximal end 10 to the distal end 20 and form a closed ring 32 as a circular receptacle in the region of the distal end 20. In the exemplary embodiment illustrated, the splints 30 and the closed ring 32 are formed in one piece from a fiber-reinforced plastics material, the receiving device 25 for the prosthetic component being embedded therein. As an alternative, the closed ring 32 can be formed as a separate component to which the splints 30 are secured. The closed ring 32 can consist of a material which differs from the material of the splints 30. In addition to a round configuration of the circular receptacle 32, the latter can be configured in an ovally or irregularly formed manner, such that a stump end or an inner socket end can be received securely. A shape adapted to the stump end can be molded individually, and it is also possible for the circular receptacle to be formed in a multipart manner, for example as a clasp which is closed via a flexible and optionally non-elastic fastening element, for example a web, such that elastic displacement toward the stump is possible to a small degree at least over a part of the height of the receptacle 32.

Provided in the proximal region of the splints 30 are fastening elements 13, 14 in the form of screws which serve to fasten an inner socket 2. Preferably, the inner socket 2 is fastened reversibly to the prosthesis socket 1 so that different inner sockets 2 can be used in the prosthesis socket 1. As a result, it is possible to be able to prefabricate the prosthesis socket 1 in a few standard sizes and at the same time to be able to supply an extraordinarily large range of patients with such a prosthesis socket 1.

A limiting element 50 in the form of a belt is fastened between the two splints 30, of which the lateral splint 30 is illustrated. The limiting element 50 is a flexible, tensionally rigid element which on the one hand allows the prosthesis socket 1 to change shape to a certain degree, and on the other hand prevents an excessive displacement of the splints 30 in the medial lateral direction. As a result, excessive expansion of the plastics material or silicone of the plastics or silicone matrix 40 is prevented. The length of the limiting element 50 can either be fixed or is settable, for example by way of a locking device.

Provided in the lateral splint 30 is a cutout 35 for an electrode, via which the myoelectric signals from the stump can be acquired. The myoelectric signals can be used to control the prosthetic component, for example a prosthetic hand.

As an alternative to the configuration with two splints 30, which are arranged medially and laterally, the prosthesis socket can also be provided with only one splint 30, which is arranged either medially or laterally and which is securable to the stump via the limiting element 50, which is disposed circularly and can be embedded at least partially in the plastics or silicone matrix 40. The limiting element 50 forms the proximal abutment, while the distal circular receptacle 32 forms the distal abutment, so that forces and moments can be transmitted effectively from the prosthesis socket to the stump. In such a configuration, too, the splint 30 is embedded in the matrix 40, which forms a cavity for receiving the stump.

Figure 2:
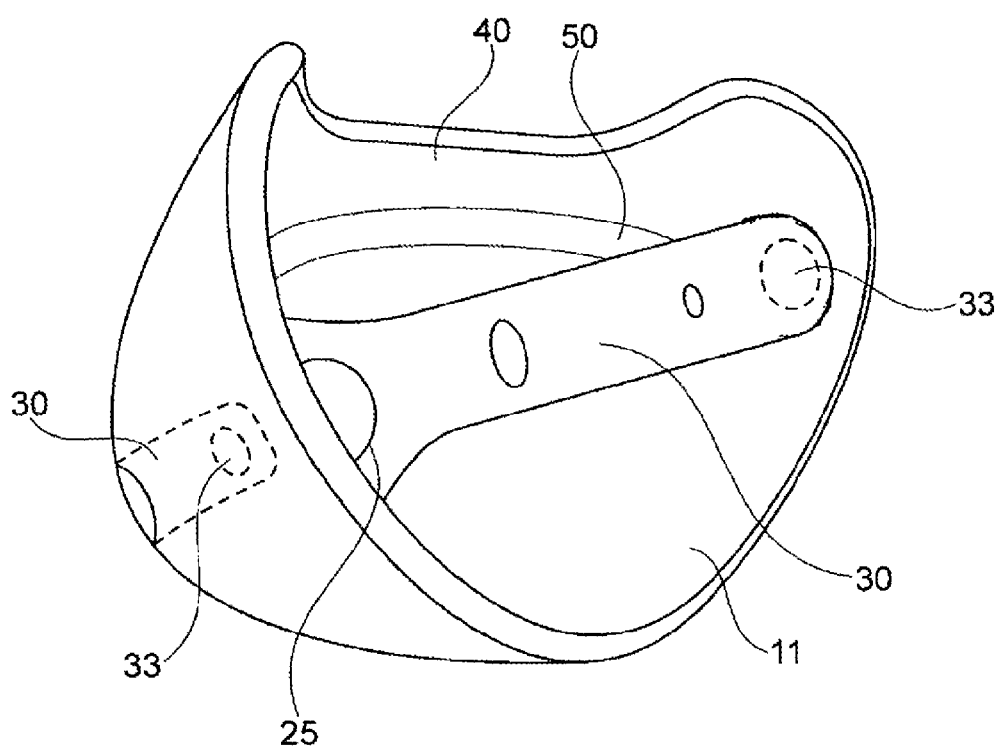
FIG. 2 shows a perspective interior view of a prosthesis socket.

FIG. 2 shows a perspective interior view of the prosthesis socket 1. The circumferentially closed formation of the plastics or silicone matrix 40 can be seen, as can the splints 30 extending along virtually the entire length of the prosthesis socket 1, said splints 30 being arranged both laterally and distally. The splints 30 are surrounded completely by the plastics or silicone matrix 40 along an exterior of the prosthesis socket 1, as clearly shown in FIGS. 1 and 2, and the splints 30 exposed along an interior of the prosthesis socket 1, as clearly shown in FIG. 1. The flexible, tensionally rigid limiting element 50, which can consist of a high-strength fabric or also of a clasp, is arranged on the top side of the splints 30 and is also surrounded completely by the plastics or silicone matrix 40 along an exterior of the prosthesis socket 1, as clearly shown in FIG. 1. The limiting element 50 is shown exposed along an interior of the prosthesis socket 1, as clearly shown in FIG. 2. At least FIGS. 1 and 2 show that splints 30 and limiting element 50 are embedded within the plastics or silicone matrix 40 with radially inward facing surfaces of the splints 30 and limiting element 50 being exposed along an inner surface of the prosthesis socket 1. The limiting element 50 is shown extending circumferentially along a curved path between the splints 30. Provided at the distal ends of the splints 30 are cambered elements 33 for receiving condyles. These cambered elements 33 are cushioned in the plastics or silicone matrix 40 on account of the complete embedding. The plastics or silicone matrix 40 can be formed in an elastic manner so that in the event of the splints 30 expanding in the medial lateral direction, a restoring force is exerted such that the splints 30 rest firmly against the stump. The splints 30 pressing against the stump are cushioned by the inner socket 2.

The receiving device 25 for the prosthetic component (not illustrated), in the present exemplary embodiment in the form of a screw thread, is illustrated at the distal end 20.

Figure 3:
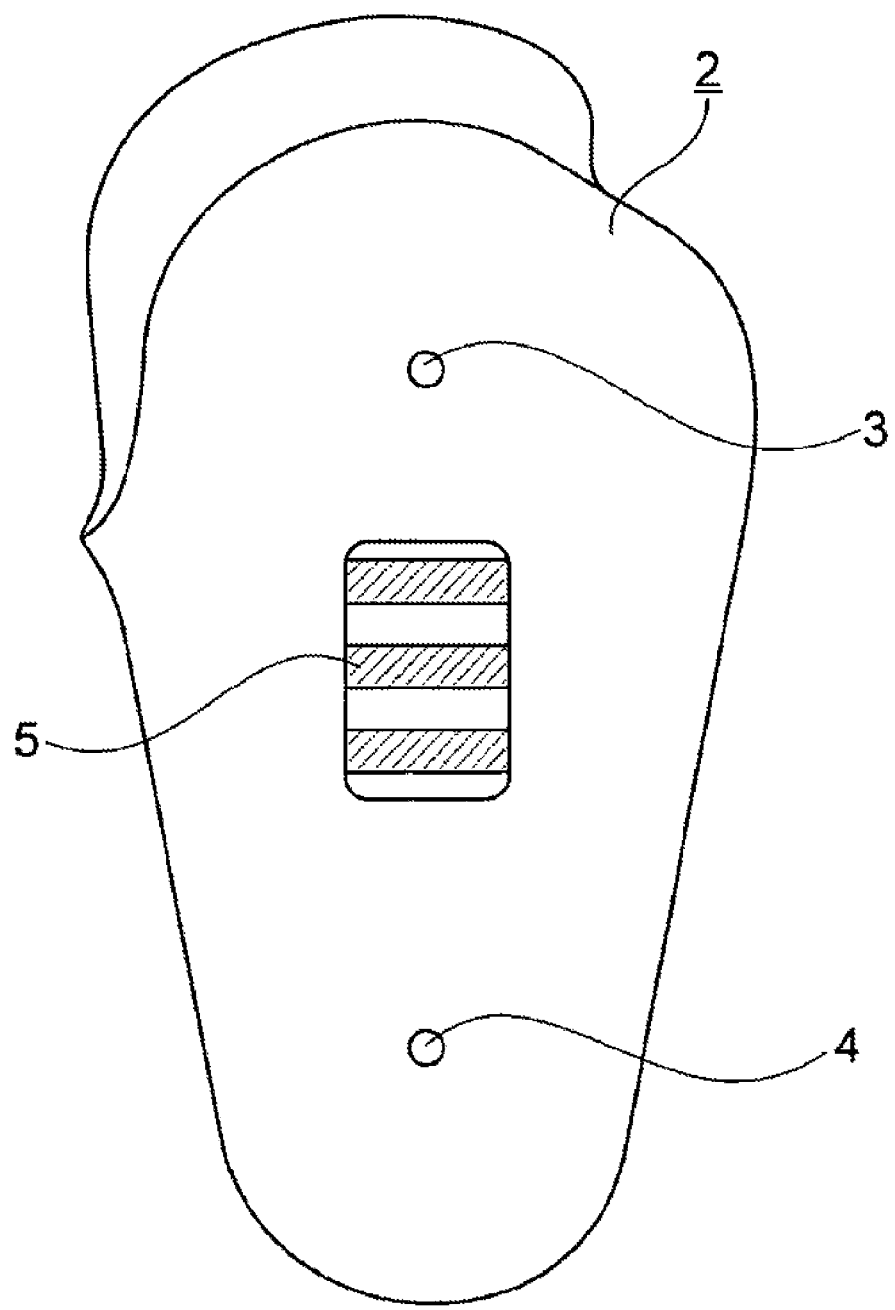
FIG. 3 shows a perspective side view of an inner socket.

FIG. 3 shows a side view of an inner socket 2 which consists of a soft, flexible and elastic material, for example silicone or polyurethane. A contact panel 5 having conductive elements for conducting myoelectric signals from the stump to the outer side of the inner socket 2 and to the inner side of the prosthesis socket 1 is provided, as are screw nuts 3, 4 which serve for fastening the inner socket 2 via the fastening elements 13, 14, in particular screws. Via the contact surfaces of the contact panel 5, the myoelectric signals are conducted to an electrode which is provided in the cutout 35 in the plastics or silicone matrix 40 and the splint 30.

Figure 4:
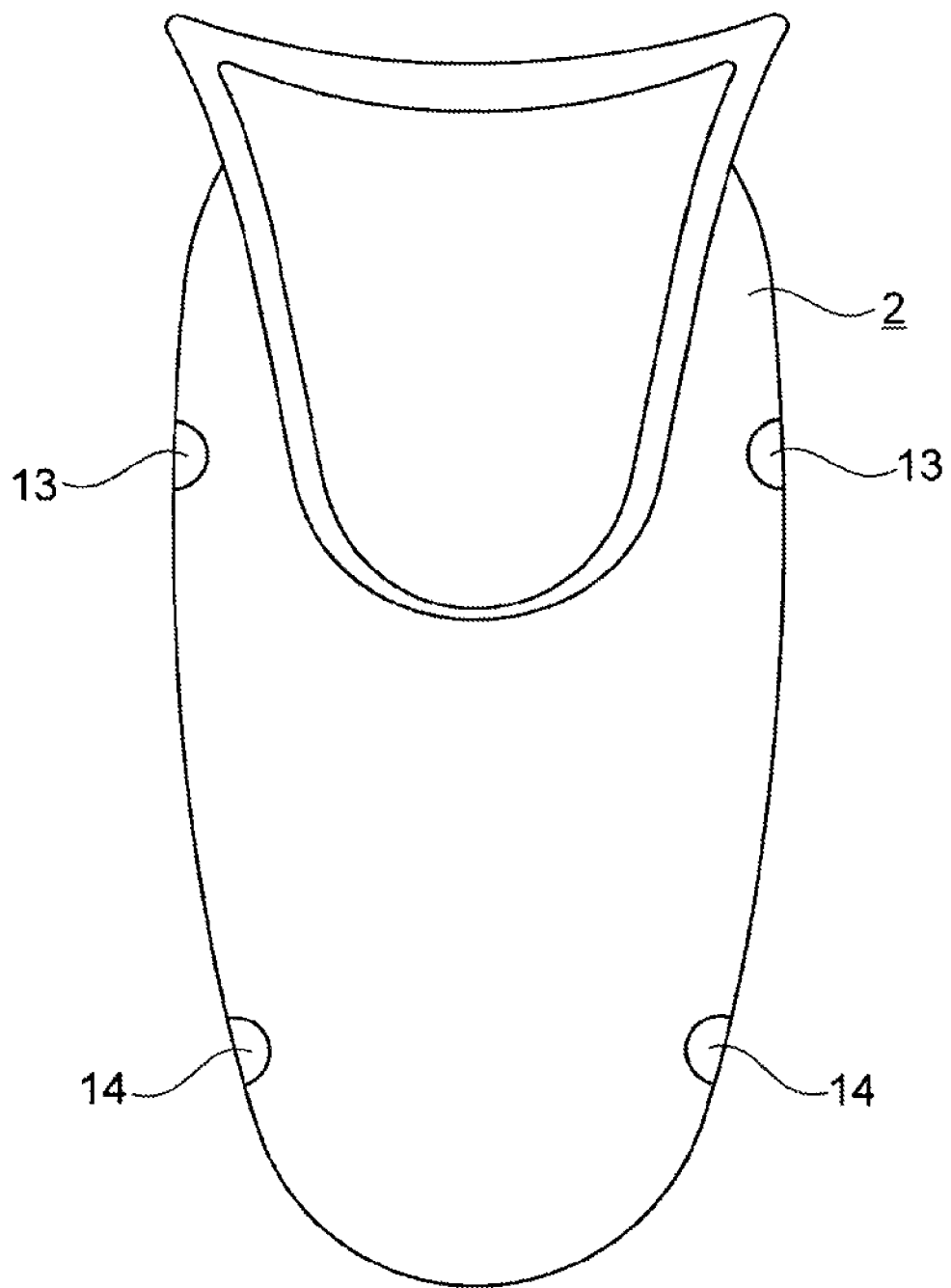
FIG. 4 shows a front view of an inner socket.

In a front view in FIG. 4, the inner socket 2 is provided for receiving a stump, in the present case a forearm stump. In each case two screw nuts 3, 4 are incorporated medially and laterally, in order to fix the inner socket 2 reversibly to the prosthesis socket 1.

The prosthesis socket 1 provides great freedom of movement and high wearing comfort for the patient, in particular by way of better adaptability of the prosthesis socket 1 to the patient. In spite of the high flexibility on account of the plastics or silicone matrix 40, high structural integrity is provided by the dimensionally stable splints 30. The combination of rigid splints 30 and a covering reduces the noises which can occur as a result of motorized drives within the prosthesis socket 1. These motorized drives are generally accommodated in the prosthesis socket 1 and serve to actuate the prosthetic component to be attached. The complete embedding in the plastics or silicone matrix 40 makes it easier to clean the prosthesis socket 1 and so the prosthesis socket 1 can be used as a test prosthesis for different patients. The inner socket 2 can be adapted or can have been adapted individually to the stump, such that the fit and the seat of the prosthesis socket 1 and thus of the prosthetic component on the stump are ensured.

The invention claimed is:

1. A prosthesis socket, comprising:
    a proximal end;
    a distal end;
    an opening at the proximal end to receive a stump;
    a receiving device for a prosthetic component positioned at the distal end;
    a flexible plastics or silicone matrix forming a hollow structure with a continuous annular perimeter configured to surround the stump;
    at least one splint made of a dimensionally stable material, the at least one splint comprising a circular receptacle in a region of the distal end, the at least one splint being embedded in the flexible plastics or silicone matrix;
    at least one flexible, tensionally rigid limiting element arranged on the at least one splint, the at least one limiting element being embedded in the flexible plastics or silicone matrix, the at least one limiting element being spaced proximal of the receiving device and extending circumferentially along a curved path between portions of the at least one splint.

2. The prosthesis socket as claimed in claim 1, wherein the prosthesis socket comprises at least two splints which are arranged in a manner spaced apart from one another and are located at least regionally opposite one another, wherein the plastics or silicone matrix at least regionally fills the spacing between the splints, thereby forming the hollow structure.

3. The prosthesis socket as claimed in claim 1, wherein the at least one splint is connected at the distal end to a closed ring or is formed in one piece, forming a closed ring.

4. The prosthesis socket as claimed in claim 1, wherein the at least one splint is formed from a fiber-reinforced plastics material.

5. The prosthesis socket as claimed in claim 1, wherein the plastics or silicone matrix is formed in an elastic manner.

6. The prosthesis socket as claimed in claim 1, wherein the plastics or silicone matrix completely surrounds the at least one splint and covers the at least one splint along an exterior of the prosthetic socket, the at least one splint being exposed along an interior of the prosthetic socket.

7. The prosthesis socket as claimed in claim 1, wherein the at least one splint has recesses to receive condyles in a region of the proximal end.

8. The prosthesis socket as claimed in claim 1, wherein the at least one splint is arranged in a manner oriented medially laterally.

9. The prosthesis socket as claimed in claim 1, wherein a flexible and elastic inner socket is secured to the at least one splint.

10. The prosthesis socket as claimed in claim 1, wherein the prosthetic socket is in the form of a forearm socket and the prosthetic component is in the form of a prosthetic hand.

11. The prosthesis socket as claimed in claim 1, wherein the at least one limiting element is arranged in a circularly disposed manner, the plastics or silicone matrix covering the at least one limiting element along an exterior of the prosthetic socket, and the at least one limiting element being exposed along an interior of the prosthetic socket.

12. A prosthesis socket, comprising:
a proximal end;
a distal end;
an opening at the proximal end to receive a stump;
a prosthetic component;
a receiving device to receive the prosthetic component at the distal end;
at least one splint, comprising:
  a dimensionally stable material;
  a circular receptacle;
a flexible plastics or silicone matrix, the plastic or silicone matrix forming a hollow structure with a continuous annular perimeter configured to surround the stump, the at least one splint being embedded in the flexible plastics or silicone matrix;
at least one flexible, tensionally rigid limiting element arranged on the at least one splint, the at least one limiting element being embedded in the flexible plastics or silicone matrix, the at least one limiting element being spaced proximal of the receiving device and extending circumferentially between portions of the at least one splint.

13. The prosthesis socket as claimed in claim 12, wherein the prosthesis socket comprises at least two splints, the at least two splints being spaced apart from one another, and the plastic or silicone matrix is positioned between the splints to form the hollow structure.

14. The prosthesis socket as claimed in claim 12, wherein the at least one splint is connected at the distal end to a closed ring or is formed in one piece, forming a closed ring.

15. The prosthesis socket as claimed in claim 12, wherein the at least one splint is formed from a fiber-reinforced plastic material.

16. The prosthesis socket as claimed in claim 12, wherein the plastic or silicone matrix is formed in an elastic manner.

17. The prosthesis socket as claimed in claim 12, wherein the plastic or silicone matrix completely surrounds the at least one splint and covers the at least one splint along an exterior of the prosthetic socket, the at least one splint being exposed along an interior of the prosthetic socket.

18. The prosthesis socket as claimed in claim 12, wherein the at least one splint has recesses to receive condyles at the proximal end.

19. The prosthesis socket as claimed in claim 12, wherein the at least one splint is oriented medially laterally.

20. The prosthesis socket as claimed in claim 12, further comprising a flexible and elastic inner socket secured to the at least one splint.

21. A prosthesis socket, comprising:
a proximal end;
a distal end;
an opening at the proximal end to receive a stump;
a receiving device for a prosthetic component positioned at the distal end;
a flexible plastics or silicone matrix forming a hollow structure with a continuous annular perimeter configured to surround the stump, the flexible plastics or silicone matrix being elastic;
at least one splint made of a dimensionally stable material, the at least one splint comprising a circular receptacle in a region of the distal end, the at least one splint being embedded in the flexible plastics or silicone matrix;
at least one flexible, tensionally rigid limiting element arranged on the at least one splint, the at least one limiting element being embedded in the flexible plastics or silicone matrix, the at least one limiting element being spaced proximal of the receiving device and extending circumferentially along a curved path between portions of the at least one splint.

22. A prosthesis socket, comprising:
a proximal end;
a distal end;
an opening at the proximal end to receive a stump;
a prosthetic component;
a receiving device to receive the prosthetic component at the distal end;
at least one splint, comprising:
  a dimensionally stable material;
  a circular receptacle;
a flexible plastics or silicone matrix, wherein the plastic or silicone matrix is formed in an elastic manner, the flexible plastics or silicone matrix forming a hollow structure with a continuous annular perimeter configured to surround the stump, the at least one splint being embedded in the flexible plastics or silicone matrix;
at least one flexible, tensionally rigid limiting element arranged on the at least one splint, wherein the limiting element is arranged in a circularly disposed manner and is embedded in the flexible plastics or silicone matrix, the at least one limiting element being spaced proximal of the receiving device and extending circumferentially along a curved path between portions of the at least one splint.

* * * * *